US006048857A

United States Patent [19]

Ellinwood, Jr. et al.

[11] Patent Number: 6,048,857

[45] Date of Patent: Apr. 11, 2000

[54] DOSING METHOD OF ADMINISTERING MEDICAMENTS VIA INHALATION ADMINISTRATION

[76] Inventors: Everett H. Ellinwood, Jr., 3519 Tonbridge Way, Durham, N.C. 27707; Samir K. Gupta, 2015 Galloping Hills Rd., Kenilworth, N.J. 07033

[21] Appl. No.: 09/009,678

[22] Filed: Jan. 20, 1998

Related U.S. Application Data

[63] Continuation-in-part of application No. 08/622,829, Mar. 27, 1996, Pat. No. 5,739,136, which is a continuation-in-part of application No. 08/321,246, Oct. 11, 1994, Pat. No. 5,504,086, which is a continuation-in-part of application No. 08/038,911, Mar. 29, 1993, Pat. No. 5,354,780, which is a continuation-in-part of application No. 07/703,049, May 17, 1991, Pat. No. 5,198,436, which is a continuation of application No. 07/422,992, Oct. 17, 1989, abandoned.

[51] Int. Cl.[7] .......... A61K 31/55

[52] U.S. Cl. .......... 514/221

[58] Field of Search .......... 514/221

[56] References Cited

U.S. PATENT DOCUMENTS

| | | | |
|---|---|---|---|
| 2,642,063 | 6/1953 | Brown | 128/206 |
| 3,807,400 | 4/1974 | Cocozza | 128/266 |
| 3,906,950 | 9/1975 | Cocozza | 128/266 |
| 3,991,761 | 11/1976 | Cocozza | 128/266 |
| 3,992,144 | 11/1976 | Jackson | 8/174 |
| 4,013,075 | 3/1977 | Cocozza | 128/266 |
| 4,167,570 | 9/1979 | Schmidt et al. | 424/256 |
| 4,371,101 | 2/1983 | Cane et al. | 222/636 |
| 4,601,897 | 7/1986 | Saxton | 424/45 |
| 4,841,964 | 6/1989 | Hurka et al. | 128/203.15 |
| 4,920,989 | 5/1990 | Rose et al. | 131/270 |
| 4,955,945 | 9/1990 | Weick | 128/203 |
| 5,016,652 | 5/1991 | Rose et al. | 131/270 |
| 5,173,298 | 12/1992 | Meadows | 424/427 |
| 5,369,117 | 11/1994 | Sallmann et al. | 514/374 |
| 5,388,572 | 2/1995 | Mulhauser et al. | 128/203.15 |
| 5,388,573 | 2/1995 | Mulhauser et al. | 128/203.15 |
| 5,394,869 | 3/1995 | Covarrubias | 128/203.29 |
| 5,415,162 | 5/1995 | Casper et al. | 128/203.12 |
| 5,503,869 | 4/1996 | Van Oort | 427/2.14 |

FOREIGN PATENT DOCUMENTS

| | | | |
|---|---|---|---|
| WO 92/00115 | 1/1992 | WIPO | A61M 15/00 |
| WO 93/24166 | 12/1993 | WIPO | A61M 15/00 |
| WO 94/20164 | 9/1994 | WIPO | A61M 15/00 |

OTHER PUBLICATIONS

Ward et al., "Pharmacokinetics and Drug Disposition—Morphine Pharmacokinetics after Pulmonary Administration from a Novel Aerosol Delivery System", *Clinical Pharmacology & Therapeutics*, vol. 62, No. 6, (Dec. 1997) pp. 596–609.

Shaw et al., "Skin as a Mode for Systemic Drug Administration", *Pharmacology of Skin II*, edited by Greaves and Shuster, chp. 13, pp. 115–122 (1989).

Southam, "Transdermal Fentanyl Therapy: System Design, Pharmacokinetics and Efficacy", *Anti–Cancer Drugs*, vol. 6, Suppl. 3, (1995) pp. 29–34.

Hung et al., "Pharmacokinetics of Inhaled Liposome–Encapsulated Fentanyl", *Anesthesiology*, vol. 83, No. 2, (Aug. 1995) pp. 277–284.

*Primary Examiner*—Zohreh Fay
*Attorney, Agent, or Firm*—Jenkins & Wilson, P.A.

[57] ABSTRACT

A method of therapeutically administering certain medicaments in order to maximize the desired effects and minimize the unwanted metabolite effects on the human body, including the central nervous system, in order to maximize therapeutic effects, such as anti-anxiety, anticonvulsant and hypnotic effects, and minimize unwanted side effects, such as ataxic and incoordination effects, of the medicament. Also, a method of inhalation administration or skin administration of certain medicaments in order to decrease metabolism of the medicaments to unwanted metabolites.

4 Claims, 10 Drawing Sheets

Figure 1. Sublingual VS Oral Q and DOQ, Single Dosing

Figure 2. Sublingual VS Oral Q and DOQ, Single Dosing

Figure 3.Sublingual VS Oral Q and DOQ,Multiple Dosing

Figure 4.Sublingual VS Oral HZ and NDZ, Single Dosing

Figure 5.Sublingual VS Oral HZ and NDZ,Single Dosing

DOSING METHOD OF ADMINISTERING MEDICAMENTS VIA INHALATION ADMINISTRATION

CROSS REFERENCE TO RELATED APPLICATIONS

This application is a continuation-in-part of application Ser. No. 08/622,829 filed on Mar. 27, 1996, now U.S. Pat. No. 5,739,136, which is a continuation-in-part of application Ser. No. 08/321,246 filed Oct. 11, 1994 and issued on Apr. 2, 1996 as U.S. Pat. No. 5,504,086 which is a continuation-in-part of application Ser. No. 08/038,911 filed on Mar. 29, 1993 and issued on Oct. 11, 1994 as U.S. Pat. No. 5,354,780, which is a continuation-in-part of application Ser. No. 07/703,049 filed on May 17, 1991 and issued on Mar. 30, 1993 as U.S. Pat. No. 5,198,436, which is a continuation application of Ser. No. 07/422,992 filed on Oct. 17, 1989 and now abandoned.

Abbreviations
The following abbreviations are employed throughout this application.

| | |
|---|---|
| meta-chlorophenylpiperazine | mCPP |
| nefazodone | NEF |
| area under the curve | AUC |
| peak plasma concentration | $C_{max}$ |
| benzodiazepine Type I | $BZ_1$ |
| benzodiazepine Type II | $BZ_2$ |
| quazepam | Q |
| N-desalkyl-2-oxoquazepam | DOQ |
| single sublingual dose | SL |
| per oral swallowed dose | PO |
| N-desalkyl-3-hydroxy-halzepam | ND |
| halazepam | HZ |
| chlorimipramine | CL |
| desmethylchlorimipramine | DMCL |
| gastrointestinal | GI |

TECHNICAL FIELD

The present invention relates to a novel method of administering certain medicaments which surprisingly results in a maximization of the effect on the human body, including the central nervous system receptors, due to the desired medicament and results in minimization of the effect on the human body, including the central nervous system receptors, due to the unwanted metabolite from the medicament. Consequently, the invention maximizes therapeutic effects, such as antianxiety, anticonvulsant, and/or hypnotic effects, and minimizes unwanted side effects, such as ataxic and incoordination effects, of the medicament.

More particularly, when certain medicaments that generate metabolites which are unwanted (the adversive metabolites are increased by gastrointestinal tract absorption and subsequent portal vein entry to the liver for instance when the medicament is orally swallowed), then, in accordance with the present invention, the intraoral, i.e., buccal or sublingual administration, of such medicaments significantly reduces change of the medicaments into unwanted metabolites.

Also, then, in accordance with the present invention, inhalation administration or skin administration of such medicaments would avoid the gastrointestinal tract absorption portal vein entry to the liver and thus, will significantly reduce change of the medicaments into unwanted metabolites.

BACKGROUND OF THE INVENTION

With respect to intraoral administration, the most pertinent prior art reference known to applicants is U.S. Pat. No. 4,229,447 to Porter which discloses a method of administering certain benzodiazepines sublingually and buccally. Porter specifically mentions the sublingual or buccal administration of diazepam, lorazepam, oxazepam, temazepam and chlorodiazepoxide and describes two generic structures of benzodiazepines that may be administered sublingually or buccally.

The compound shown below is contemplated by the generic structures in Porter. All of the benzodiazepines disclosed and the generic structure described in Porter are $BZ_1$-$BZ_2$ receptor non-specific since they lack the trifluoro ethyl group pendant at the N position of the "B" ring which confers $BZ_1$ specificity.

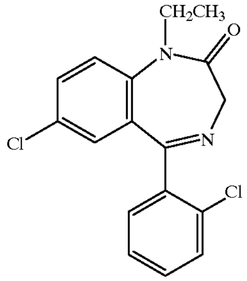

Porter's method is based on the rapid buccal or sublingual absorption of selected benzodiazepines to attain effective plasma concentration more rapidly than oral administration. In contrast, while parenteral administration provides a rapid rise of blood levels of the benzodiazepines, parenteral administration is frequently accompanied by pain and irritation at the injection site and may require sterilization of the preparatives and the hypodermic syringes.

Porter points out that the intraoral, i.e., buccal or sublingual administration, of lipid soluble benzodiazepines results in therapeutic levels resembling parenteral administration without some of the problems associated with parenteral administration. Porter's administration technique for benzodiazepines in general builds on a long established knowledge in pharmacology that a drug absorbed in the intraoral route gives rise to more rapid absorption than the same drug swallowed into the stomach. What is not recognized by Porter, however, are concerns with first-pass metabolism which can be avoided either with the sublingual or parenteral route of drug administration of certain benzodiazepines.

Porter does not recognize that first-pass metabolism designates the drug intestinal absorption with subsequent entry directly into the portal blood supply leading to the liver and that the liver in turn rapidly absorbs and metabolizes the drug with its first-pass high concentration through the liver. In addition, some first pass metabolism may occur during the absorption process into the intestine. Thus, large amounts of the drug may never be seen by the systemic circulation or drug effect site. Porter further does not recognize that the more rapid metabolism via the first-pass metabolism route can lead to accelerated desalkylation with formation of high plasma concentrations of an unwanted metabolite.

Thus, applicants' concern with avoiding the degradation of the parent compound and its desired positive effect and avoiding the metabolism of the parent compound to an undesired metabolite is neither recognized nor addressed by Porter, who only addresses the ability of the oral mucous membranes to absorb certain benzodiazepines fast and achieve high plasma levels of these benzodiazepines quickly.

The specific drug for which this phenomenon was demonstrated by Porter was lorazepam which has a simple metabolism that results in it not being metabolized to active compounds. Also, and very significantly, the issue of human nervous system receptor specificity and activation for $BZ_1$ and $BZ_2$ type receptors is not recognized by Porter either generally or with reference specifically to trifluorobenzodiazepines.

U.S. Pat. No. 3,694,552 to Hester discloses that 3-(5-phenyl-3H-1,4-benzodiazepine-2-yl) carbazic acid alkyl esters, which are useful as sedatives, hypnotics, tranquilizers, muscle relaxants, and anticonvulsants, can be administered sublingually. Subsequently issued U.S. Pat. No. 4,444,781 to Hester specifically teaches that 8-chloro-1-methanol-6-(o-chlorophenyl)-4H-s-triazolo [4,3-a][1,4]-benzodiazepine therapeutic compounds, which are useful as soporifics, can be suitably prepared for sublingual use.

Also, U.S. Pat. No. 4,009,271 to vonBebenburg et al. discloses that 6-aza-3H-1,4-benzodiazepines and 6-aza-1,2-dihydro-3H-1,4-benzodiazepines (which have pharmacodynamic properties including psychosedative and anxiolytic properties as well as antiphlogistic properties) can be administered enterally, parenterally, orally or perlingually.

The chemical formula of nefazodone is 2-(3-(4-(3-chlorophenyl)-1-piperazinyl)propyl-5-ethyl-2,4-dihydro-4-(2-phenoxyethyl)-3H-1,2,4-triazol-3-one hydrochloride and it is abbreviated as NEF.

Patients with obsessive compulsive disorder respond to meta-chlorophenylpiperazine (abbreviated as mCPP), an undesirable metabolite of NEF, by becoming much more anxious and obsessional, as reported by Zohar et al. in "Serotonergic Responsivity in Obsessive Compulsive Disorder: Comparison of Patients and Healthy Controls", *Arch. Gen. Psychiatry,* Vol. 44, pp. 946–951 (1987). The peak in the anxiousness and obsessional behaviors is observed within 3 hours of mCPP administration and the duration of the worsening ranges from several hours to as much as 48 hours. Much more significantly, mCPP induced a high rate of emergence of entirely new obsessions or the reoccurrence of obsessions that had not been present in the patients for several months. Patients also reported being more depressed and dysphoric.

More specifically, Zohar et al. administered 0.5 mg/kg of mCPP orally to subjects in eliciting their obsessional symptoms. The peak plasma concentration in the control patients was 33.4±17.34 ng/ml, whereas, in the obsessional patients, the peak plasma concentration inducing the obsessional behavior was 26.9 ng/ml±12.33.

Furthermore, Hollander et al., in "Serotonergic Noradrenergic Sensitivity in Obsessive Compulsive Disorder: Behavioral Findings", *Am. J. Psychiatry,* Vol. 1945, pp. 1015–1017, (1988), have reported many of these obsessional worsening effects in obsessive compulsive patients.

Additionally, Kahn et al., in "Behavioral Indications for Serotonin Receptor Hypersensitivity in Panic Disorder", *Psychiatry Res.,* Vol. 25, pp. 101–104 (1988), have reported mCPP induces anxiety in a group of panic disorder patients.

Moreover, Walsh et al., as reported in "Neuroendocrine and Temperature Effects of Nefazodone in Healthy Volunteers", *Biol. Psychiatry,* Vol. 33, pp. 115–119 (1933), administered oral doses of 50 mg and 100 mg of NEF to normal subjects and measured NEF and its metabolite mCPP. For the 50 mg dose, the NEF/mCPP area under the curve (abbreviated as AUC) ratio was 1.58. For the 100 mg dose, the AUC ratio was 1.63, indicating that within the first 3 hours, NEF is substantially metabolized to mCPP at levels considerably above the mCPP levels that Zohar et al., supra, found to induce anxiety and obsessional states in susceptible individuals.

In studies in dogs, intravenous dosing of NEF reduced plasma mCPP Cmax by 50% from that found with oral dosing, as reported by Shukla et al., in "Pharmacokinetics, Absolute Bioavailability, and Disposition of [$^{14}C$] Nefazodone in the Dog", *Drug Metab. Disposition,* Vol. 21, No. 3, pp. 502–507 (1993).

Also, a discussion of bupropion and its three major metabolites, erythrohydrobupropion, hydroxybupropion, and threohydrobupropion, as well as the strong relationship of higher hydroxybupropion metabolite concentrations in therapeutically non-responding patients in contrast to responders, can be seen in Posner et al., "The Disposition of Bupropion and Its Metabolites in Healthy Male Volunteers after Single and Multiple Doses", Vol. 29, *Eur. J. Clin. Pharmacol.,* pp. 97–103 (1985) and Bolden et al., "Bupropion in Depression", Vol. 45, *Arch. Gen. Psychiatry,* pp. 145–149 (February 1988). Hydroxybupropion, therefore, represents an unwanted metabolite.

Background information with respect to skin administration of drugs is as follows.

In one embodiment of the present invention, use of skin (i.e., transdermal) administration as a primary vehicle for administration of drugs to bypass the GI tract absorption and portal vein entry into the liver is contemplated.

Highly lipid soluble substances are absorbed through the skin and even are the basis for the toxicity for such lipid soluble drugs as the insecticides and organic solvents. Absorption through the skin can be enhanced by suspending the drug in an oily vehicle and rubbing it onto the skin, a method known as inunction.

A variety of improvements in transdermal administration of drugs has transpired over the last few years.

For example, ultrasound mediated transdermal delivery, in which low frequency ultrasound application increases the permeability of the skin to many drugs including higher molecular weight drugs, was recently described by Mitragotri, Blankschtein, and Langer in "Ultrasound-Mediated Transdermal Protein Delivery", *Science,* 269:850–853 (1995).

In addition, when ionizable drugs such as dexamethasone sodium phosphate or lidocane hydrochloride are used, the electro-transport system of iontophoresis can be used to drive the drugs through the skin such as in the use of the PHORESOR® made by IOMED. Also, Alza Corporation has also been active in developing electro-transport systems for drug delivery. (See, Alza U.S. Pat. D384,745 issued Oct. 7, 1997; D372,098 issued Jul. 23, 1996; U.S. Pat. No. 5,629,019 issued May. 13, 1997; and Ser. No. 566,817 issued Sep. 16, 1997. The disclosures of these patents are incorporated herein by reference.)

The advantages of skin administration to the systemic circulation include:

1) bypassing the gastrointestinal portal vein entry into the liver and its first-pass metabolism, 2) sustained blood levels without multiday dosing, and 3) blood concentrations of drug controllable within and between patients in a narrow range See, Shaw, J. E. and Chandrasekaran, S. K., "Skin as a Mode for Systemic Drug Administration", Greaves, M. W. and Shuster, S. (eds), *Pharmacology of the Skin II,* Springer-Verlag:New York, pp. 115–122 (1989).

Background information with respect to skin patches, a preferred embodiment, is described as follows.

For instance, administration of nicotine by way of a skin patch can be seen in U.S. Pat. No. 4,920,989 to Rose, Jarvik, and Rose, and in U.S. Pat. No. 5,016,652 to Rose and Jarvik.

Of the rapid development of techniques for administering drugs by skin patches, one improvement is the development by Fuisz Technology LTD of a melt spinable carrier agent such as sugar which is combined with a medicament and then converted to a fiber for by melt-spinning. (See, U.S. Pat. No. 4,855,362, entitled "Rapidly Dissolvable Medicinal Dosage Unit and Method of Manufacture".) This facilitates dissolving the medication onto any surface area when wetted such as with skin moisture. It is also readily applicable to sublingual or buccal administration.

These skin delivery systems are well known to those practiced in the art of clinical pharmacology. The disclosures of these patents regarding skin patches are incorporated herein by reference. (See also, Southam, M. A., "Transdermal Fentanyl Therapy: System Design, Pharmacokinetics and Efficacy", *Anti-Cancer Drugs,* 6 Suppl. 3:29–34, (1995) as an example of skin patches.)

Background information with respect to inhalation of drugs is as follows.

Inhalation techniques for administering drugs have been known for centuries. Witness the use of smoking to administer opiates and nicotine.

Also, inhalation of gases is a classical means of inducing surgical anesthesia and as well volatile drugs may be inhaled in this manner.

In another embodiment of the present invention, the focus is on inhalation administration of medicaments, particularly via inhalators, such as for dry powders or aerosols. As with skin drug administration, inhalation drug administration provides a means of bypassing the gastrointestinal portal vein entry first-pass metabolism and as well provides a means of rapid access to the general circulation. See, Benet, L. Z., Kroetz, D. L. and Sheiner, L. B., "Pharmacokinetics: The Dynamics of Drug Absorption, Distribution, and Elimination", Hardman, L. G. et al. (eds), *Goodman and Gilman's The Pharmacological Basis of Therapeutics,* $9^{th}$ Ed, McGraw-Hill:New York, pp. 3–27, (1996).

Drugs delivered from inhalators are airborne fine particles. The particles may be aerosolized suspensions (admixed with a propellant gas, i.e., a chlorofluorocarbon) or may be dispersed powders (generally admixed with an excipient). These particles may be either liquids or solids and are defined by the mass median aerodynamic diameter (MMAD). Thus, solid particulate(s) and liquid droplet(s) with the same unit density have the same average rate of settling (e.g., in the lungs).

The size of the airborne particles is important. If they are larger than 10 micrometers diameter, they are unlikely to reach the lungs for deposit. If they are smaller than 0.5 micrometers diameter, they may be exhaled again.

One of the problems with inhalation delivery is that only approximately 10–20% of the drug is delivered to the lung alveoli. The rest is deposited into the oro-pharynx. If this were swallowed, it would go into a gastrointestinal absorption portal vein liver entry and metabolism pathway. Thus, mouth rinsing is frequently recommended.

In the present invention, this deposition into the oropharynx does not present the same type of problem. Since the airborne drug being inhaled is in a fine particle form with the appropriate formulation, it will be rapidly absorbed in the oral cavity if swallowing is delayed as it will with sublingual administration. Thus, inhalation administration presents a combined buccalingual pathway (as well as an oropharyngeal pathway) plus the lung absorption means of bypassing the gastrointestinal liver first-pass metabolism.

There are several inhalator delivery systems contemplated as useful in the present invention.

One is a traditional nebulizer which works via a mechanism similar to the familiar perfume atomizer. The airborne particles are generated by a jet of air from either a compressor or compressed gas cylinder passing through the device. In addition, newer forms utilize an ultrasonic nebulizer by vibrating the liquid at speeds of up to about 1 MHZ.

Another type of inhalator delivery system is the metered dose inhaler (MDI). This has been widely used because of its convenience and usually contains a suspension of the drug in a aerosol propellant. However, the MDI has fallen into disfavor recently due to problems with chlorofluorocarbon propellants causing depletion of the earth's ozone layer, which has led to increased use of still another type of inhalator delivery system, namely the dry powder inhaler.

The typical dry powder inhaler has the appropriate dose often placed in a capsule along with a flow aid or filler excipient, such as large lactose or glucose particles. Inside the device, the capsule is initially either pierced by needles (SPINHALER®) or sheered in half (ROTOHALER®). Propellers turning cause the capsule contents to enter the air stream and to be broken up into small particles. (See also, DISKHALER®, TURBUHALER®, plus numerous other dry powder inhalation delivery devices.) For a review, see Taburet, A. M. and Schmit, B., "Pharmacokinetic Optimisation of Asthma Treatment", *Clin. Pharmacokinet.,* 26(5) :396–418 (1994).

More recently, Inhale Therapeutic Systems has created an inhalator delivery system that integrates customized formulation and proprietary fine powder processing and packaging technologies with their proprietary inhalation device for efficient reproducible deep-lung delivery. Their process of providing agglomerate composition compounds of units of aggregated fine particles and methods for manufacture and use of the units has recently been covered by a series of patents. The particle size containing the drug is in the optimum range for deep-lung delivery and has a suitable friability range. The U.S. patents covering these methods include U.S. Pat. No. 5,458,135 issued Oct. 17, 1996, U.S. Pat. No. 5,607,915 issued Mar. 4, 1997 and U.S. Pat. No. 5,654,007 issued Aug. 5, 1997. (See also, U.S. Pat. No. 5,655,516 issued Aug. 12, 1997.) The disclosures of these patents are incorporated herein by reference.

Other potential improvements of pulmonary inhalation of drugs via an inhalator delivery system include the use of liposomes (microscopic phospholipid vesicles). The liposomal delivery of drugs slows the uptake of drug absorption from the lungs thus, providing a sustained drug release. (See, Hung, O. R., Whynot, S. C., Varvel, J. R., Shafer, S. L. and Mezel, M., "Pharmacokinetics of Inhaled Liposome-Encapsulated Fentanyl", *Anesthesiol.,* 82:277–284 (1995).

The key factor to be considered here is that most inhalation delivery devices are currently used for treatment of lung conditions in which it is important to supply the active drug to a site in the lungs where the drug acts for a period of time before being absorbed into the general circulation. Since the lungs have a surface area of at least the size of a tennis court and a series of thin cell sacks (alveoli) that are highly vascularized, the lungs provide a large surface area for absorption of drugs. However, in the present invention, the inhalation technique provides a means of not only administering drugs to the lungs, but also, because of the small particle size, a means of delivering highly absorbable small particles to multiple sites in the oropharyngeal pathway. Thus, the drug is dispersed to a topographically much larger mucosal absorption area than would occur from sublingual and/or buccal administration, and additionally, provided is the 10–20% absorption by lung administration.

Moreover, general background information with respect to dry powder inhalers can be seen in U.S. Pat. No. 2,642,063 to Brown; U.S. Pat. No. 3,807,400 to Cocozza; U.S. Pat. No. 3,906,950 to Cocozza; U.S. Pat. No. 3,991,761 to Cocozza; U.S. Pat. No. 3,992,144 to Jackson; U.S. Pat. No. 4,013,075 to Cocozza; U.S. Pat. No. 4,371,101 to Cane and Farneti; U.S. Pat. No. 4,601,897 to Saxton; U.S. Pat. No. 4,841,964 to Hurka and Hatschek; U.S. Pat. No. 4,955,945 to Weick; U.S. Pat. No. 5,173,298 to Meadows; U.S. Pat. No. 5,369,117 to Sallmann, Gschwind, and Francotte; U.S. Pat. No. 5,388,572 to Mulhauser, Karg, Foxen, and Brooks; U.S. Pat. No. 5,388,573 to Mulhauser and Karg; U.S. Pat. No. 5,394,869 to Covarrubias; U.S. Pat. No. 5,415,162 to Casper, Taylor, Leith, Leith, and Boundy; U.S. Pat. No. 5,503,869 to Van Oort; International Publication No. WO 92/00115 to Gupte, Hochrainer, Wittekind, Zierenberg, and Knecht; International Publication No. WO 94/20164 to Mulhauser and Karg; and International Publication No. WO 93/24166 to Wright, Seeney, Hughes, Revell, Paton, Cox, Rand, and Pritchard. The disclosures of all of these background patents vis-a-vis drug inhalers are incorporated herein by reference.

SUMMARY OF OBJECTS OF THE INVENTION

It is well known by those practiced in the art that special distribution of enzymatic activity within the gastrointestinal tract and the liver leads to a metabolic zonation for metabolism of drugs. This zonation is noted not only in the GI tract, but also in peripheral midzonal and pericentral regions of the liver.

Thus, the relative distribution of two or more enzymes with respect to substrate entry point and the relative magnitudes of the enzymatic parameters will have a large impact on the metabolic pathway emphasized. When a drug is swallowed, each of the stomach and the small intestine absorbs it, presenting an opportunity for partial metabolism with subsequent flow to the portal vein entry to the liver. Therefore, differential metabolic zonation is possible if the drug is absorbed by the gastrointestinal tract and distributed to the liver by the portal vein, rather than by the hepatic artery from the general circulation.

Even though this general background information is known to those persons practiced in the art, the specific findings that formation of unwanted metabolites is reduced by sublingual/buccal administration was not known until applicants' unexpected discovery. Also, that formation of unwanted metabolites will be reduced by inhaler administration and/or skin administration was not anticipated until applicants' present invention.

Hence, in accordance with the present invention, provided is an improvement in a method for administering medicament to the human body, including the central nervous system, wherein a therapeutically effective amount of said medicament is administered to a human by an administration selected from the group consisting of inhalation administration, skin administration, and combinations thereof. The improvement comprises selecting a medicament that is metabolized into an unwanted or adversive metabolite which is increased by gastrointestinal tract absorption and subsequent portal vein entry to the liver; and placing the medicament in a suitable (i.e., inhalation or skin) formulation. Then, a therapeutically effective amount of the formulation is administered by way of an inhalation administration and/or a skin administration so as to bypass the gastrointestinal tract absorption and subsequent portal vein entry to the liver and thereby to decrease formation of the unwanted metabolite. Next, the ratio is increased of medicament to the unwanted metabolite made available to the human body, including the central nervous system, and this method is utilized over a period of one or more doses to achieve sustained high levels of the medicament relative to the unwanted metabolite.

Also, the specific findings that trifluorobenzodiazepine N-desalkylation is reduced by non-oral administration was not known until applicants' unexpected discovery with quazepam and halazepam.

Therefore, also in accordance with the present invention, applicants provide a novel method for maximizing the effect of selected trifluorobenzodiazepines including 7-chloro-1-(2,2,2-trifluoroethyl)-5-(o-fluoro phenyl)-1,3-dihydro-2H-1,4-benzodiazepine-2-thione (i.e., quazepam) and 7-chloro-1,3-dihydro-5-phenyl-1-1-(2,2,2-trifluoroethyl)-2H-1,4-benzodiazepine-2-one (i.e., halazepam) on benzodiazepine Type I ($BZ_1$) receptors and minimizing the unwanted potent effect of certain metabolites on benzodiazepine Type II ($BZ_2$) receptors of the human central nervous system so as to maximize the antianxiety and anticonvulsant and/or hypnotic effects and to minimize the ataxic and incoordination effects thereon. The method comprises selecting a suitable lipid soluble and $BZ_1$ specific trifluorobenzodiazepine, placing the trifluorobenzodiazepine in a suitable inhalation and/or skin formulation, and then administering a therapeutically effective amount of said formulation by inhalation administration and/or by skin administration so as to bypass the first pass metabolism of said selected trifluorobenzodiazepine in the liver.

The selected trifluorobenzodiazepines with $BZ_1$ specificity are represented by the following structural formula and include:

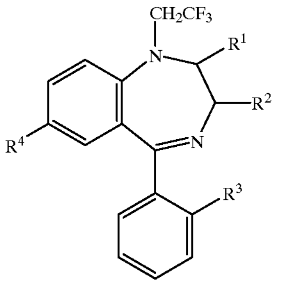

| COMPOUND | $R^1$ | $R^2$ | $R^3$ | $R^4$ |
|---|---|---|---|---|
| 1. HALAZEPAM | =O | H,H | H | Cl |
| 2. 3-OH-HALAZEPAM | =O | OH,H | H | Cl |
| 3. QUAZEPAM | =S | H,H | F | Cl |
| 4. 2-OXO-Q | =O | H,H | F | Cl |
| 5. 2-OXO-3-OH-Q | =O | OH,H | F | Cl |
| 6. SCH 15698 | H,H | H,H | F | Cl |
| 7. SCH 16893 | H,H | H,H | Cl | Cl |
| 8. SCH 18449 | H,H | H,H | F | Br |
| 9. 3-OH-Q | =S | OH,H | F | Cl |

1. 7-chloro-1-(2,2,2-trifluoroethyl)-5-phenyl-1,3-dihydro-2H-1,4-benzodiazepine-2-one.
2. 7-chloro-1-(2,2,2-trifluoroethyl)-5-phenyl-1,3-dihydro-3-hydroxy-2H-1,3-benzodiazepine-2-one.
3. 7-chloro-1-(2,2,2-trifluoroethyl)-5-(2-fluorophenyl)-1,3-dihydro-2H-1,4-benzodiazepine-2-thione.
4. 7-chloro-1-(2,2,2-trifluoroethyl)-5-(2-fluorophenyl)-1,3-dihydro-2H-1,4-benzodiazepine-2-one.

5. 7-chloro-1-(2,2,2-trifluoroethyl)-5-(2-fluorophenyl)-1,3-dihydro-3-hydroxy-2H-1,4-benzodiazepine-2-one.
6. 7-chloro-1-(2,2,2-trifluoroethyl)-5-(2-fluorophenyl)-1,3-dihydro-2H-1,4-benzodiazepine.
7. 7-chloro-1-(2,2,2-trifluoroethyl)-5-(2-chlorophenyl)-1,3-dihydro-2H-1,4-benzodiazepine.
8. 7-bromo-1-(2,2,2-trifluoroethyl)-5-(2-fluorophenyl)-1,3-dihydro-2H-1,4-benzodiazepine.
9. 7-chloro-1-(2,2,2-trifluoroethyl)-5-(2-fluorophenyl)-1,3-dihydro-3-hydroxy-2H-1,4-benzodiazepine-2-thione.

The trifluorobenzodiazepines referenced above are also lipid soluble. All of the benzodiazepines reported to have $BZ_1$ specificity have a $CH_2CF_3$ group on the nitrogen in the "B" ring. Metabolic loss of this $CH_2CF_3$ group results in a benzodiazepine that is non-specific for the $BZ_1$-$BZ_2$ receptors. Applicants' invention was made possible by the unexpected and surprising discovery from pharmacokinetic studies that sublingual dosing minimizes the desalkylation metabolic pathway leading to the formation of non-specific metabolites of the selected trifluorobenzodiazepine. It is well known by those practiced in the art of pharmacokinetics that inhalation and/or skin administration, like buccal and/or sublingual administration, also bypasses the gastrointestinal absorption and subsequent portal vein entry into the liver. Thus, the pharmacokinetic profile of dosing, by inhalation administration and/or skin administration, demonstrates that bypassing gastrointestinal absorption and portal vein liver entry will minimize the desalkylation metabolic pathway leading to the formation of non-specific metabolites of the selected trifluorobenzodiazepine.

An object of the present invention is to increase the effectiveness of certain selected trifluorobenzodiazepines on human subjects to reduce anxiety and convulsions.

Another object of the present invention is to provide a new administration method which increases the availability of certain selected trifluorobenzodiazepines to the human central nervous system and decreases the amount of undesirable metabolites available to the human central nervous system.

Still another object of the present invention is to maximize the effect of certain selected trifluorobenzodiazepines on $BZ_1$ receptors of the human central nervous system and to minimize their effect on $BZ_2$ receptors.

Some of the objects of the invention having been stated above, other objects will become evident as the description proceeds, when taken in connection with the accompanying drawings as best described below.

DETAILED DESCRIPTION OF THE INVENTION

Figure 1:
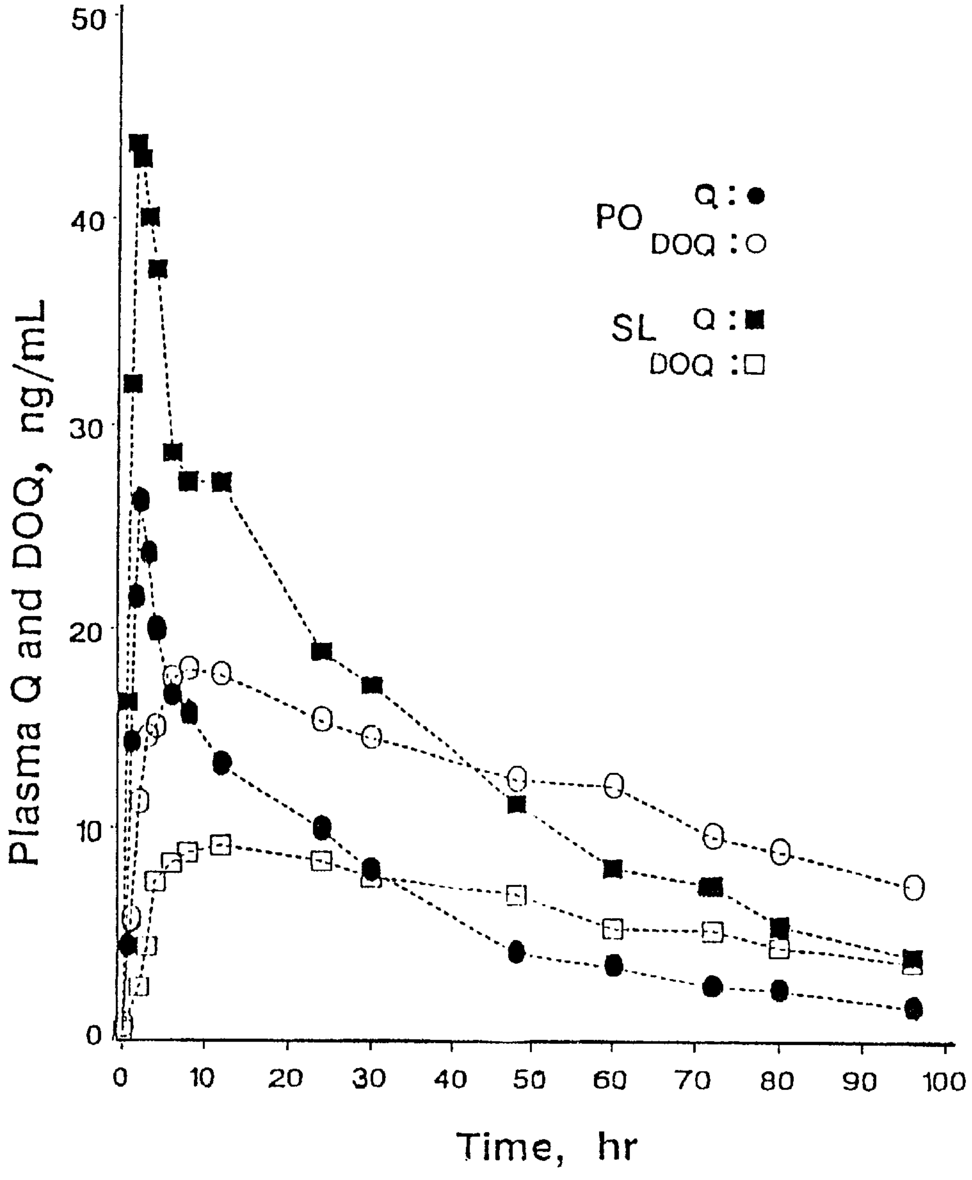
FIG. 1 is a graph illustrating the concentration of quazepam (Q) and N-desalkyl-2-oxoquazepam (DOQ) in the blood plasma over 96 hours following a single sublingual dose (SL) or per oral swallowed dose (PO) of 15 mg of quazepam.

When certain medicaments that generate metabolites which are toxic and thus unwanted (the adversive metabolites are increased by gastrointestinal tract absorption and subsequent portal vein entry to the liver, for instance when the medicament is orally swallowed), then, in accordance with the present invention, the intraoral, i.e., buccal or sublingual administration, of such medicaments significantly reduces change of the medicaments into unwanted or toxic metabolites. Based on the well known bypass of gastrointestinal portal vein liver entry, the same reduction will also be true for inhalation administration or skin administration of the medicament.

Suitable medicaments useful in accordance with the present invention are those that have the properties of:

(1) an unwanted metabolite, and (2) the ratio of the unwanted metabolite to the therapeutic drug is substantially reduced by sublingual or buccal administration, in contrast to administration by swallowing, and likewise, the ratio of the unwanted metabolite to the therapeutic drug will be substantially reduced by inhalation administration and/or skin administration, in contrast to administration by swallowing.

Examples of such suitable medicaments include, but are not limited to, a medicament selected from the group consisting of propoxyphene, trifluorobenzodiazepine, nefazodone, trazodone, chlorimipramine, bupropion, and combinations thereof.

More specifically, quazepam, a trifluorobenzodiazepine, is selective for benzodiazepine Type I ($BZ_1$) receptors of the central human nervous system. Action at the $BZ_1$ receptors has been linked to antianxiety and anticonvulsant and/or hypnotic effects, whereas action at $BZ_2$ receptors of the human central nervous system has been linked to muscle relaxation and ataxic effects. N-desalkyl-2-oxoquazepam (DOQ), an active metabolite of quazepam (Q), is $BZ_1$, $BZ_2$ receptor non-specific, and also has a much higher affinity or potency for both receptor types when compared to the $BZ_1$ specific affinity of quazepam (Q). Thus, the higher affinity metabolite (DOQ) of quazepam (Q) contributes substantially to the adverse ataxic and incoordination effects of quazepam (Q) on the human central nervous system.

In addition, because DOQ has a much longer elimination half-life than the parent compound Q, repeated dosing of Q leads to the gradual accumulation of the non-specific, unwanted metabolite, and a greater ratio of DOQ/Q attains over a period of days. Thus, after 2 or 3 hours subsequent to an acute dose of Q, the DOQ metabolite, both because of its increased gradual accumulation and its greater potency than the parent compound Q, can obviate the advantages of Q itself.

Applicants have unexpectedly and surprisingly discovered that sublingual dosing, in contrast to the usual clinical oral dosing of Q, increases the availability of Q about 60% while the DOQ drops to about ½ that of the oral Q administration levels. In other words, applicants have unexpectedly and surprisingly discovered that the aforementioned undesirable "first pass" augmentation of desalkylation to the DOQ metabolite can be markedly reduced or obviated by sublingual dosing of Q.

Figure 2:
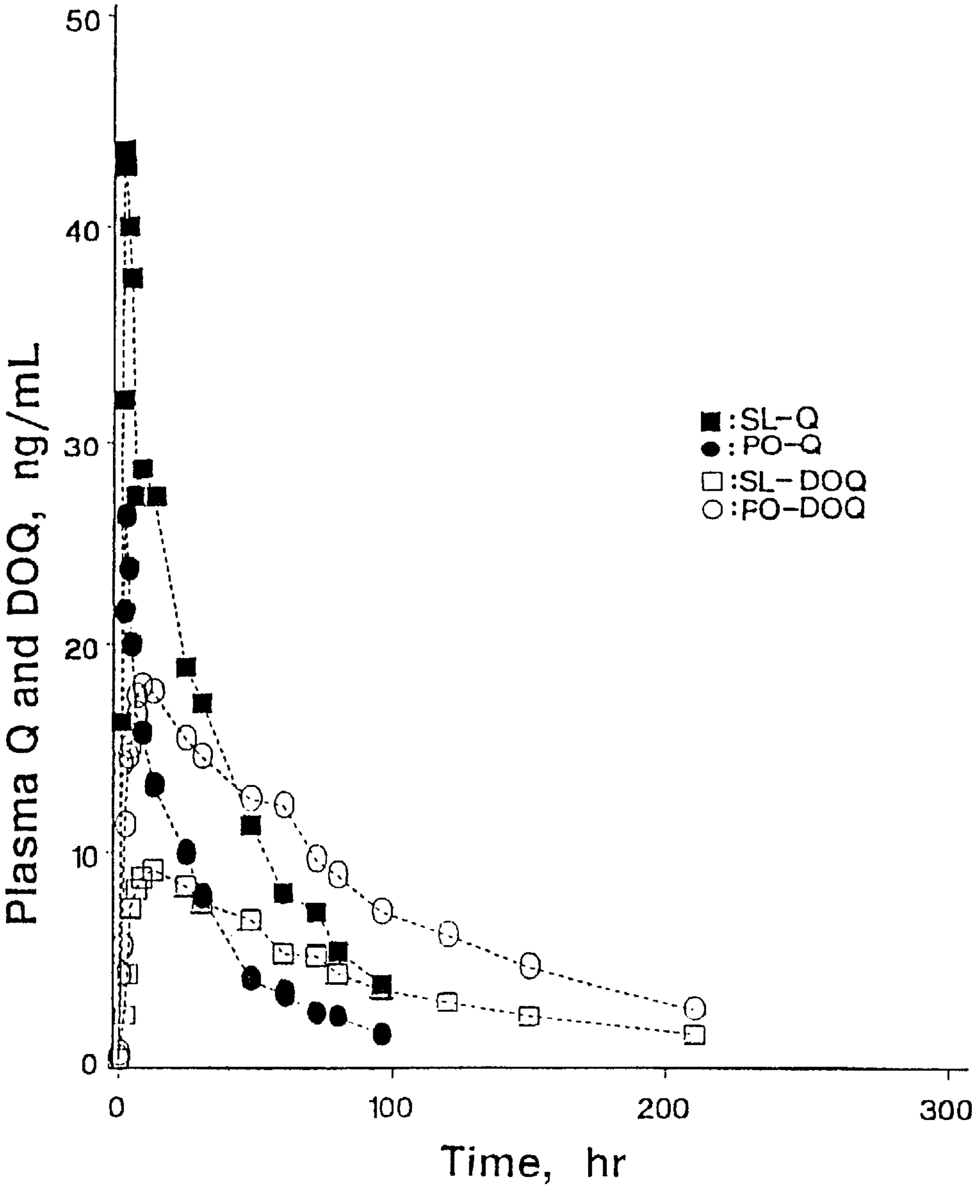
FIG. 2 is a graph illustrating the concentration of quazepam (Q) and N-desalkyl-2-oxoquazepam (DOQ) in the blood plasma over 210 hours following a single sublingual dose (SL) of 15 mg of quazepam or per oral swallowed dose (PO)

This change in concentrations for the two compounds can be seen with reference to FIG. 1 and FIG. 2 of the drawings where the differences in the parent compound Q and the metabolite DOQ for both the oral and sublingual dosing is shown.

Figure 3:
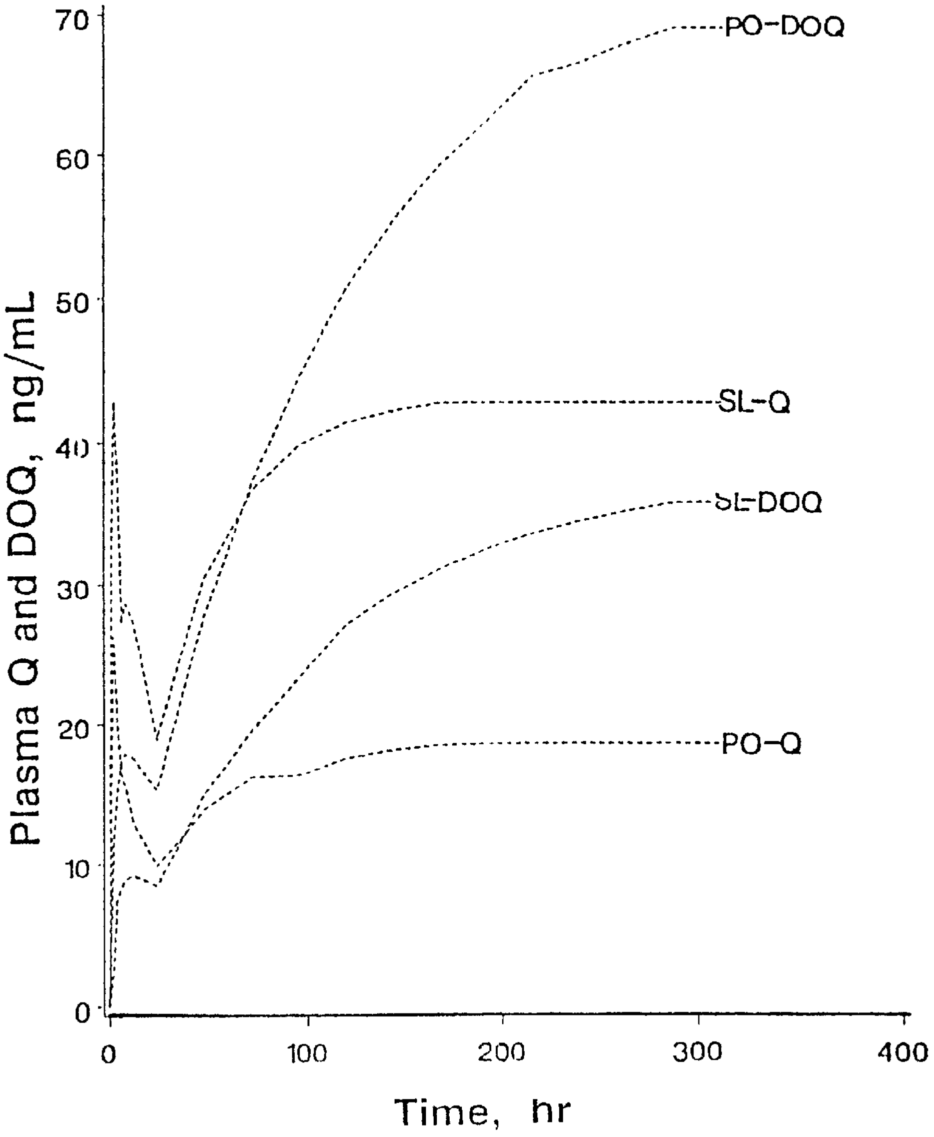
FIG. 3 is a graph of computer simulated concentration levels of Q and DOQ in the blood following sublingual and oral swallowed doses of 15 mg of Q once a day for a 15 day period illustrating the marked reduction in accumulated levels of DOQ with sublingual dosing.

In FIG. 3, by use of standard multiple Q dose simulations, the differences in accumulation of Q and DOQ for sublingual versus oral dosing over 15 days is shown. With chronic dosing it is readily apparent that after 15 days the DOQ level, following oral administration, has reached levels that are associated with the threshold for impairing ataxic and incoordination affects (especially if larger doses are given). With sublingual dosing the accumulated levels of DOQ are approximately ½ of the oral dosing and the levels of Q are over twice that of the oral levels.

In Table 1 and Table 2, set forth below, the average pharmacokinetic parameters for both Q and DOQ for both oral and sublingual routes of administration are reported:

TABLE I

AVERAGE PHARMACOKINETIC PARAMETERS OF QUAZEPAM FOLLOWING SUBLINGUAL AND ORAL ADMINISTRATION OF QUAZEPAM (15 mg)

| | Route of Adminstration of Quazepam | |
|---|---|---|
| Parameter | Sublingual | Oral |
| $t_{1/2}$ $K_a$ (hr) | 0.27 ± 0.10[a] | 0.77 ± 0.23 |
| $t_{1/2}$ λ1 (hr) | 1.44 ± 0.45 | 1.73 ± 0.65 |
| $t_{1/2}$ λ2 (hr) | 27.72 ± 7.18 | 24.63 ± 8.35 |
| Lag time (hr)[b] | 0.18 ± 0.05 | 0.52 ± 0.28 |
| $C_{max}$ (ng/ml)[b] | 42.35 ± 10.43 | 26.74 ± 6.83 |
| $t_{max}$ (hr)[b] | 0.78 ± 0.31 | 2.57 ± 1.69 |

TABLE I-continued

AVERAGE PHARMACOKINETIC PARAMETERS OF QUAZEPAM FOLLOWING SUBLINGUAL AND ORAL ADMINISTRATION OF QUAZEPAM (15 mg)

| | Route of Adminstration of Quazepam | |
|---|---|---|
| Parameter | Sublingual | Oral |
| AUC (ng · hr/ml)[b] | 1461.35 ± 298.67 | 472.79 ± 238.92 |
| CL/F (1/hr)[b] | 8.78 ± 5.25 | 37.56 ± 16.89 |

[a]Mean ± SD
[b]Differed significantly from oral dosing ($P < 0.05$)
Legend: $t_{1/2}$ = Half-Life
$K_a$ = Absorption
λ1 = Rapid Distribution
λ2 = Terminal Elimination
$C_{max}$ = Peak Plasma Concentration
$t_{max}$ = Time to $C_{max}$
AUC = Area Under Plasma Concentration Time-Curve
CL/F = Clearance

TABLE II

AVERAGE PHARMACOKINETIC PARAMETERS OF N-DESALKYL-2-OXOQUAZEPAM FOLLOWING SUBLINGUAL AND ORAL ADMINISTRATION OF QUAZEPAM (15 mg)

| | Route of Adminstration of Quazepam | |
|---|---|---|
| Parameter | Sublingual | Oral |
| $t_{1/2}$ $K_a$ (hr) | 1.07 ± 0.31[a] | 1.24 ± 0.52 |
| $t_{1/2}$ λ2 (hr) | 69.30 ± 18.62 | 71.44 ± 21.56 |
| Lag time (hr) | 1.74 ± 0.86 | 0.66 ± 0.32 |
| $C_{max}$ (ng/ml)[b] | 8.18 ± 2.35 | 17.58 ± 4.17 |
| $t_{max}$ (hr) | 7.33 ± 4.15 | 6.17 ± 3.52 |
| AUC (ng · hr/ml)[b] | 949.02 ± 365.74 | 1966.70 ± 410.90 |

[a]Mean ± SD
[b]Differed significantly from oral dosing ($P < 0.05$)
Legend: $t_{1/2}$ = Half-Life
$K_m$ = Formation
λ2 = Terminal Elimination
$C_{max}$ = Peak Plasma Concentration
$t_{max}$ = Time to $C_{max}$
AUC = Area Under Plasma Concentration Time-Curve The profile in FIGS. 1 and 2 of the drawings clearly shows that there is a first-pass metabolism for Q leading to the attenuated Q levels. On the basis of applicants' pharmacokinetic studies, applicants have discovered that sublingual dosing, which bypasses first-pass metabolism, minimizes the N-desalkylation metabolic pathway that leads to the formation of the unwanted metabolite, DOQ. This has led applicants to the sublingual dosing method of the invention which provides for maximization of the important therapeutic effects of the drug. Thus, applicants have discovered the means by which quazepam can be administered such that one can maximize the $BZ_1$ effect and reduce the $BZ_2$ effect of its metabolite DOQ and thereby enhance the efficacy in use on humans of this therapeutic drug.

In summary, applicants have discovered the following: (1) the use of sublingual dosing of Q to reduce markedly the first-pass metabolism of the Q structure and thereby to enhance the $BZ_1$ effect of the drug; and (2) the use of sublingual dosing to increase the $BZ_1$ to $BZ_2$ ratio with acute dosing and repeated dosing over days (since the dosing regimen is reducing the DOQ levels and thus attenuating the many impairing effects of the high affinity slowly metabolized Q metabolite). These phenomena resulting from sublingual dosing provide for an unexpected and surprising enhancement of the efficacy and reduction of toxicity of the drug in reducing anxiety and convulsions in humans.

Applicants believe that essentially the same results as discussed above for the sublingual administration of Q should be obtained for the inhalation administration and/or skin administration of Q (i.e., marked reduction in the first-pass metabolism of Q and increase in the $BZ_1$ to $BZ_2$ ratio), as compared to the oral administration of Q.

Figure 4:
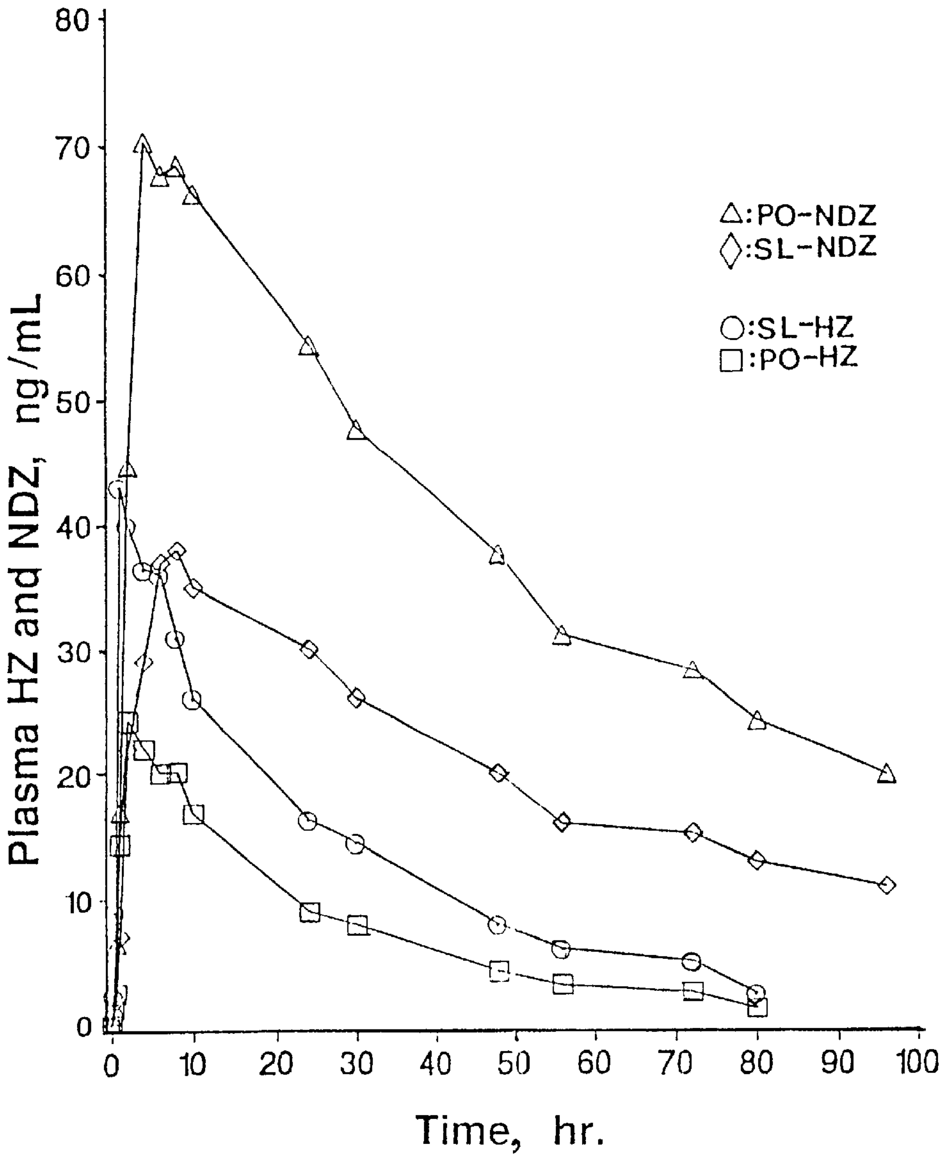
FIG. 4 is a graph illustrating the concentration of halazepam (HZ) and N-desalkyl-3-hydroxy-halazepam (ND) in the blood over 96 hours following a single sublingual dose (SL) or per oral swallowed dose (PO) of 20 mg of halazepam.
Figure 5:
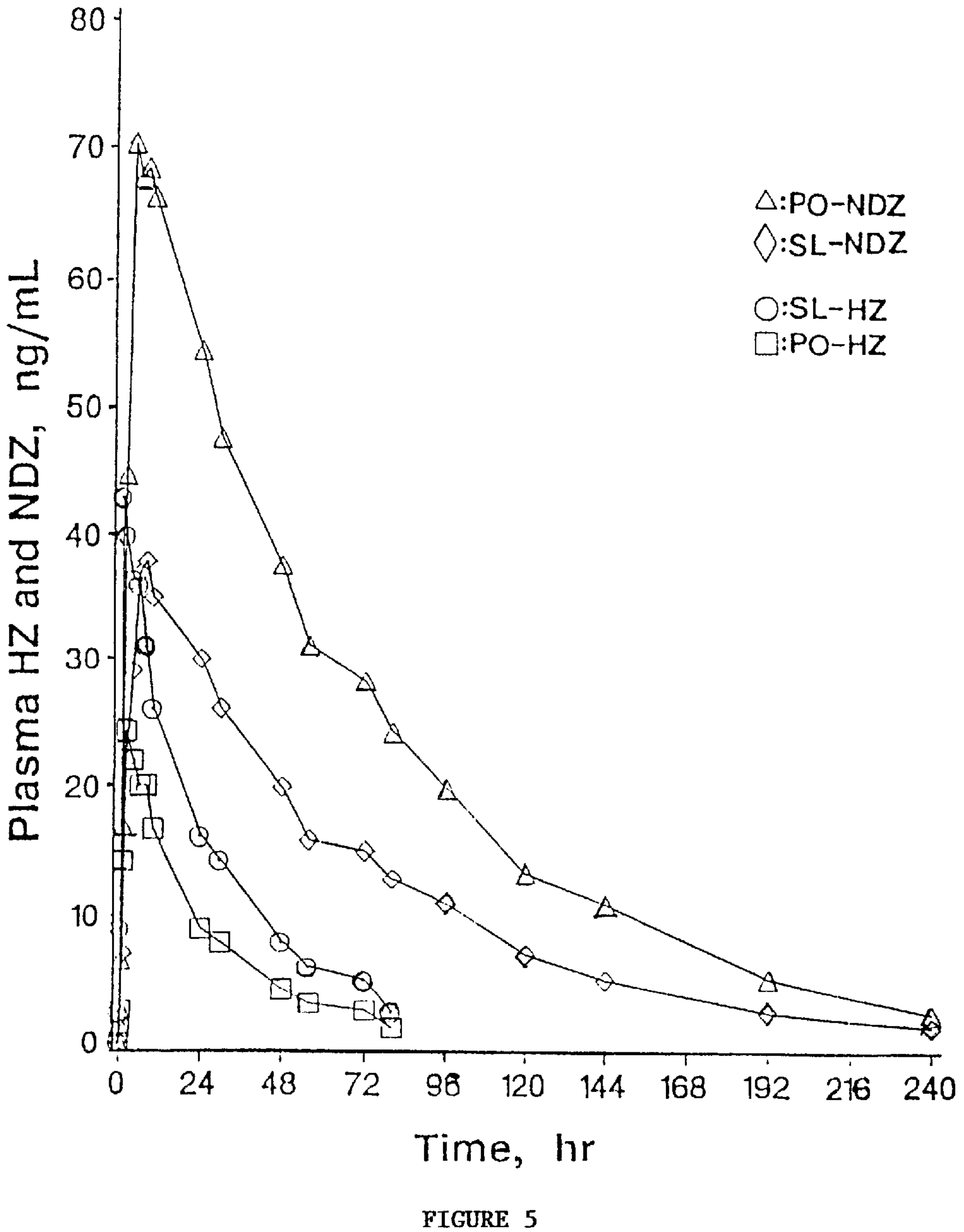
FIG. 5 is a graph illustrating the concentration of halazepam (HZ) and N-desalkyl-3-hydroxy-halazepam (ND) in the blood over 240 hours following a single sublingual dose (SL) or per oral swallowed dose (PO) of 20 mg of halazepam.

With reference now to FIGS. 4 and 5, applicants have also tested the high $BZ_1$ specific drug halazepam and discovered similar results obtained by sublingual administration of this drug. More particularly, the availability of halazepam was significantly increased thus maximizing the $BZ_1$ effect while reducing the $BZ_2$ metabolite N-desalkyl-hydroxy-halazepam.

Based on the pharmacokinetic knowledge well known to those skilled in the art, essentially the same results as discussed above for the sublingual administration of HZ will be obtained for the inhalation administration and/or skin administration of HZ (i.e., marked reduction in the first-pass metabolism of HZ and increase in the $BZ_1$ to $BZ_2$ ratio), as compared to the oral administration of HZ.

Intraoral administration, either buccal or sublingual, and likewise inhalation administration and/or skin administration, of selected trifluorobenzodiazepines can substantially enhance their therapeutic effect for the reasons set forth.

Figure 6:
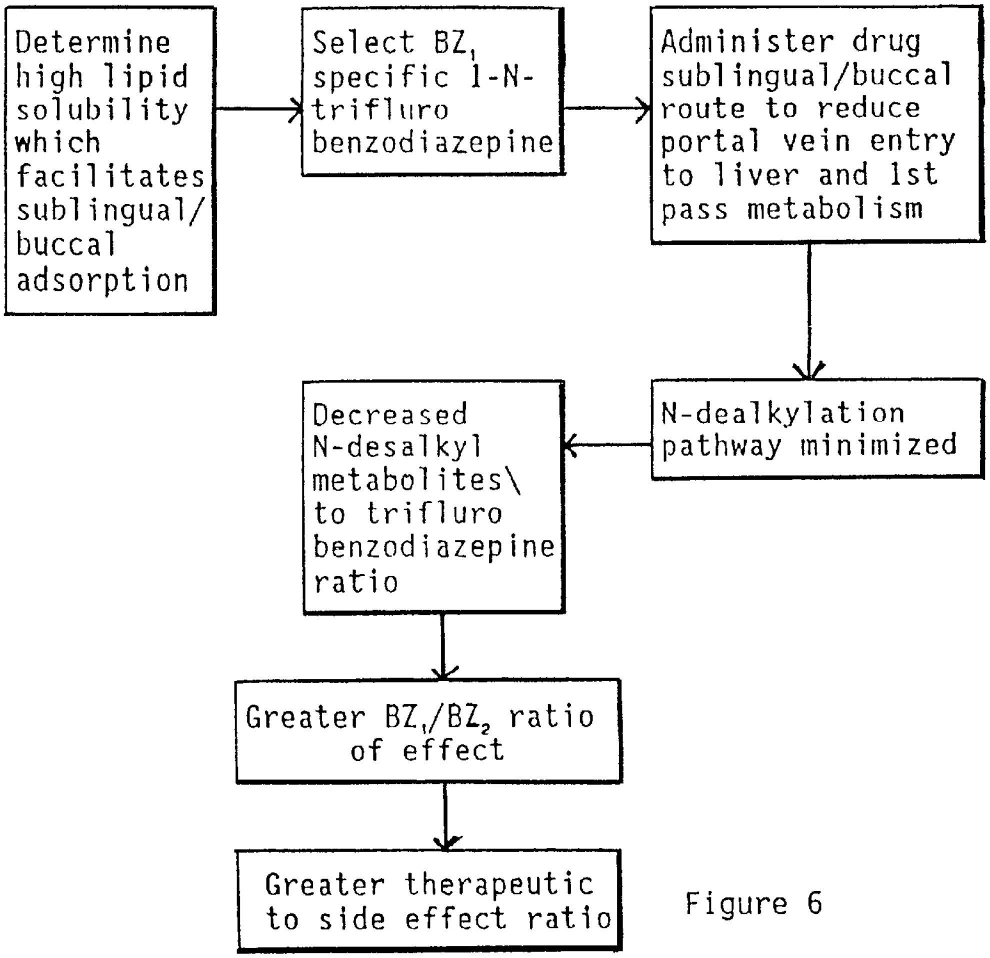
FIG. 6 is a flow chart of the method of the present invention with respect to sublingual/buccal absorption.

Applicants' novel method can be better appreciated with reference to FIG. 6 of the drawings which depicts a flow chart of the steps of the novel therapeutic method for sublingual/buccal administration, and applicants believe essentially the same results will be obtained for inhalation administration and/or skin administration.

Alternative Embodiment of the Invention

Applicants have shown above that the manner in which the original blood borne trifluorobenzodiazepine drug enters into the liver has a profound effect on directing the vector of metabolism for this given species of drugs. This class of benzodiazepines has a desalkylation metabolism.

Applicants' findings of the alteration of metabolism by sublingual administration led to the novel discovery that one could alter the steady state metabolic profile of this class of drugs by bypassing the profound early stage desalkylation metabolism that occurred when the swallowed drug entry was via the gastrointestinal absorption and portal vein metabolic pathway. This discovery required projection of acute dosing pharmacokinetics to understand fully and to project steady state pharmacokinetics that document the robust advantages of the sublingual administration route in: (1) shifting to a reduced desalkylation metabolic profile; (2) reducing the production of unwanted non-specific metabolites; and (3) thereby, enhancing an advantageous ratio $BZ_1$ specific to the non-specific $BZ_1$, $BZ_2$ metabolites.

Since the original discovery described above that N-desalkylation of trifluorobenzodiazepines could be markedly reduced by sublingual administration, applicants have now discovered that desalkylation of other drugs can be reduced by sublingual or buccal administration. Applicants likewise submit that essentially the same results will be obtained for inhalation administration and/or skin administration of these other drugs. These other drugs also have unwanted or toxic desalkylation metabolites.

For example, propoxyphene (the formula of which is (+)-α-4-(dimethylamino)-3-methyl-1,2-diphenyl-2-butanol propionate hydrochloride), is a widely used, prescribed, oral analgesic that is frequently associated with poisonings and death. A major concern is that accumulating levels of the non-analgesic metabolite norpropoxyphene has cardiac conduction depressing effects that are a source of cardiotoxicity. The wanted analgesic effects of propoxyphene are limited by its short half-life, whereas, the unwanted norpropoxyphene metabolite has a half-life of 2 to 3 times that of the propoxyphene. With multiple dosing, the norpropoxyphene metabolite half-life may increase to 39 hours, thus accumulating over days of use.

Propoxyphene is N-desalkylated similarly to the trifluorobenzodiazepines. Since its desalkylated metabolite norpropoxyphene has the potential to induce cardiac conduction delay with toxic consequences at accumulated doses, applicants explored the sublingual route of administration. Two normal subjects were given 65 mg of propoxyphene both by per oral swallowed and sublingual administration.

Figure 7:
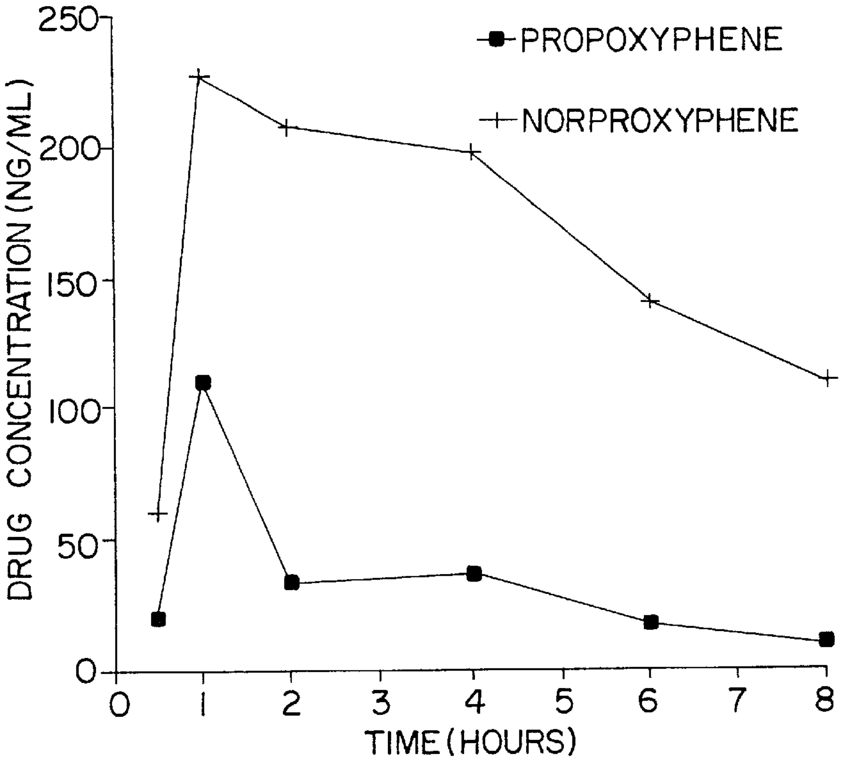
FIG. 7 is a graph illustrating the concentration of propoxyphene and norpropoxyphene in the blood plasma over 8 hours following a single per oral swallowed dose of 65 mg of propoxyphene.
Figure 8:
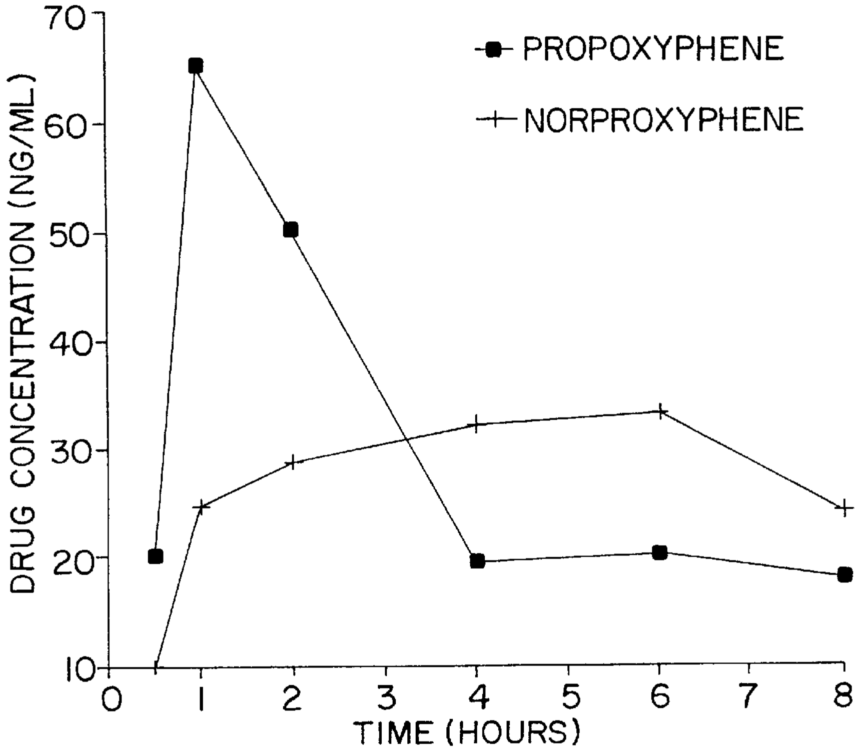
FIG. 8 is a graph illustrating the concentration of propoxyphene and norpropoxyphene in the blood plasma over 8 hours following a single sublingual dose of 65 mg of propoxyphene in the same subject as seen in FIG. 7.
Figure 9:
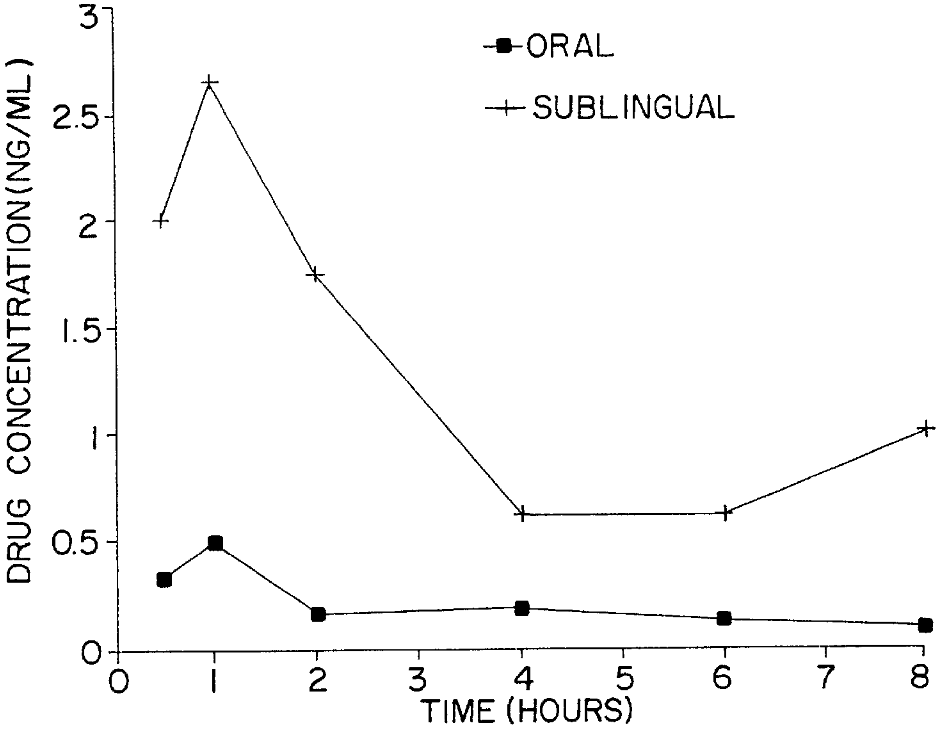
FIG. 9 is a graph illustrating the ratio of propoxyphene concentration to norpropoxyphene concentration for both per oral swallowed and sublingual administration in the subject seen in FIGS. 7 and 8.
Figure 10:
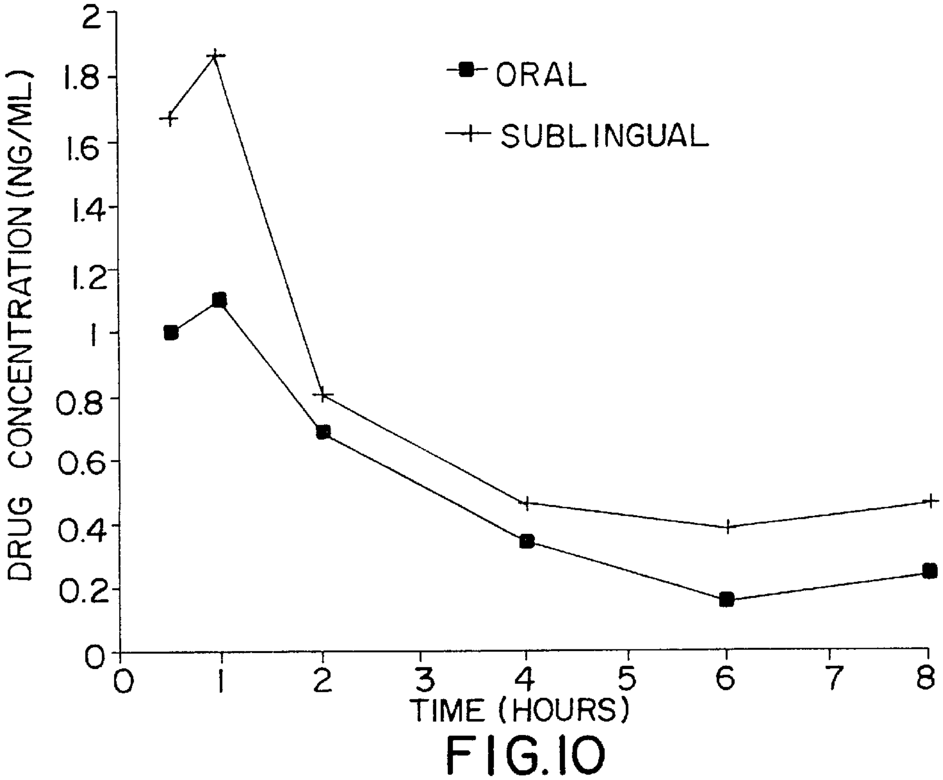
FIG. 10 is a graph illustrating the ratio of propoxyphene concentration to norpropoxyphene concentration for both per oral swallowed and sublingual administration in another subject in addition to that shown in FIGS. 7 and 8.

FIGS. 7 and 8 demonstrate the propoxyphene and norpropoxyphene plasma concentrations for (1) per oral swallowed and (2) sublingual administration, respectively, in a single subject over a respective 8 hour period for each type of administration. FIG. 9 illustrates the propoxyphene/norpropoxyphene ratios for sublingual and oral dosing over time for the subject of FIGS. 7 and 8. FIG. 10 illustrates the same ratios for a second subject under the same test conditions. The increase in wanted parent compound to unwanted metabolite for sublingual dosing is readily apparent. Thus, sublingual dosing reduces propoxyphene desalkylation metabolism thereby increasing the therapeutic to toxic ratio.

Applicants submit that essentially the same results as discussed above for the sublingual administration of propoxyphene will be obtained for the inhalation administration and/or skin administration of propoxyphene.

As a further example, another drug that has N-desalkylation to an unwanted metabolite is chlorimipramine (CL) which is metabolized to desmethylchlorimipramine (DMCL).

CL is a specific inhibitor of serotonin uptake which is a desired property in the treatment of obsessive compulsive disorders, whereas DMCL is a potent inhibitor of norepinephrine. Therefore, the DMCL metabolite in many individuals accumulates to levels much greater than CL, and thus qualitatively changes the biochemical effect during treatment. In addition, the accumulation of DMCL poses additional potential toxicity from its cardiac conduction slowing properties similar to that of norproxyphene.

Applicants administered 25 mg of CL to normal subjects per orally and sublingually. In subjects who had a high desalkylation level, sublingual administration markedly reduced the unwanted metabolite DMCL thereby increasing the wanted parent compound CL to unwanted metabolite DMCL ratio. Other subjects did not demonstrate this effect. Therefore, the sublingual administration would be important only for certain individual patients who were shown to have unfavorable ratios.

Applicants submit that essentially the same results as discussed above for the sublingual administration of CL will be obtained for the inhalation administration and/or skin administration of CL.

Second Alternative Embodiment of the Invention

In a study of mCPP plasma levels that were achieved by oral dosing of human subjects with nefazodone (mCPP is an unwanted metabolite of nefazodone, abbreviated as NEF), the area under the curve from 1 hour to 6 hours for two subjects revealed a NEF/mCPP ratio of 1.93, slightly higher than the ratio described by Walsh et al., supra. In contrast, sublingual administration of NEF (which included an incidental amount of buccal administration) to human subjects resulted in a NEF/mCPP ratio from 1 hour to 6 hours of 3.82.

Thus, approximately a 100% increase in the ratio of wanted to unwanted metabolites was achieved with sublingual administration of NEF, as compared to oral administration of NEF, and the same magnitude of increase should also be achieved with buccal administration of NEF. Because NEF and mCPP have a short half-life, values after 6 hours have little contribution to the plasma levels. The plasma levels before 1 hour were variably below the detection level and/or highly variable so they were not included in the values reported.

More importantly, the peak mCPP plasma levels (hereinafter, abbreviated $C_{max}$) were considerably more elevated from the oral dosing versus the sublingual dosing. One subject had a peak level of 51 ng/ml for sublingual dosing compared to 145 ng/ml for oral dosing. The other subject had a 21 ng/ml $C_{max}$ mCPP level for sublingual dosing versus a 48 ng/ml mCPP for oral dosing. Thus, the $C_{max}$ levels for mCPP were approximately 3 times greater for the oral dosing than for the sublingual dosing. These values are significant in that Zohar et al., supra, reported that levels of 26–35 ng/ml induced obsessional and anxiolytic effects, in obsessional patients.

To compare sublingual to oral administration, the mean average values for the two subjects for mCPP for sublingual administration (SL) and for oral administration (PO) at 1 to 6 hours, are reported below in Table III.

TABLE III

PHARMACOKINETICS OF NEFAZODONE (NEF) AND mCPP AFTER 50 mg SUBLINGUAL AND ORAL OF NEF

| | Subject 1 | | | | Means for Both Subjects | | | |
|---|---|---|---|---|---|---|---|---|
| Parameters | NEF SL | PO | mCPP SL | PO | NEF SL | PO | mCPP SL | PO |
| $C_{max}$ (ng/ml) | 200 | 291 | 21 | 48 | 174 | 226 | 33 | 97 |
| $AUC_{6hr}$ (ng · hr/ml) | 568 | 420.3 | 44 | 84.3 | 435.5 | 521 | 114 | 270 |

The abbreviations used in Table III are the same as those used in Tables I and II above.

Figure 11:
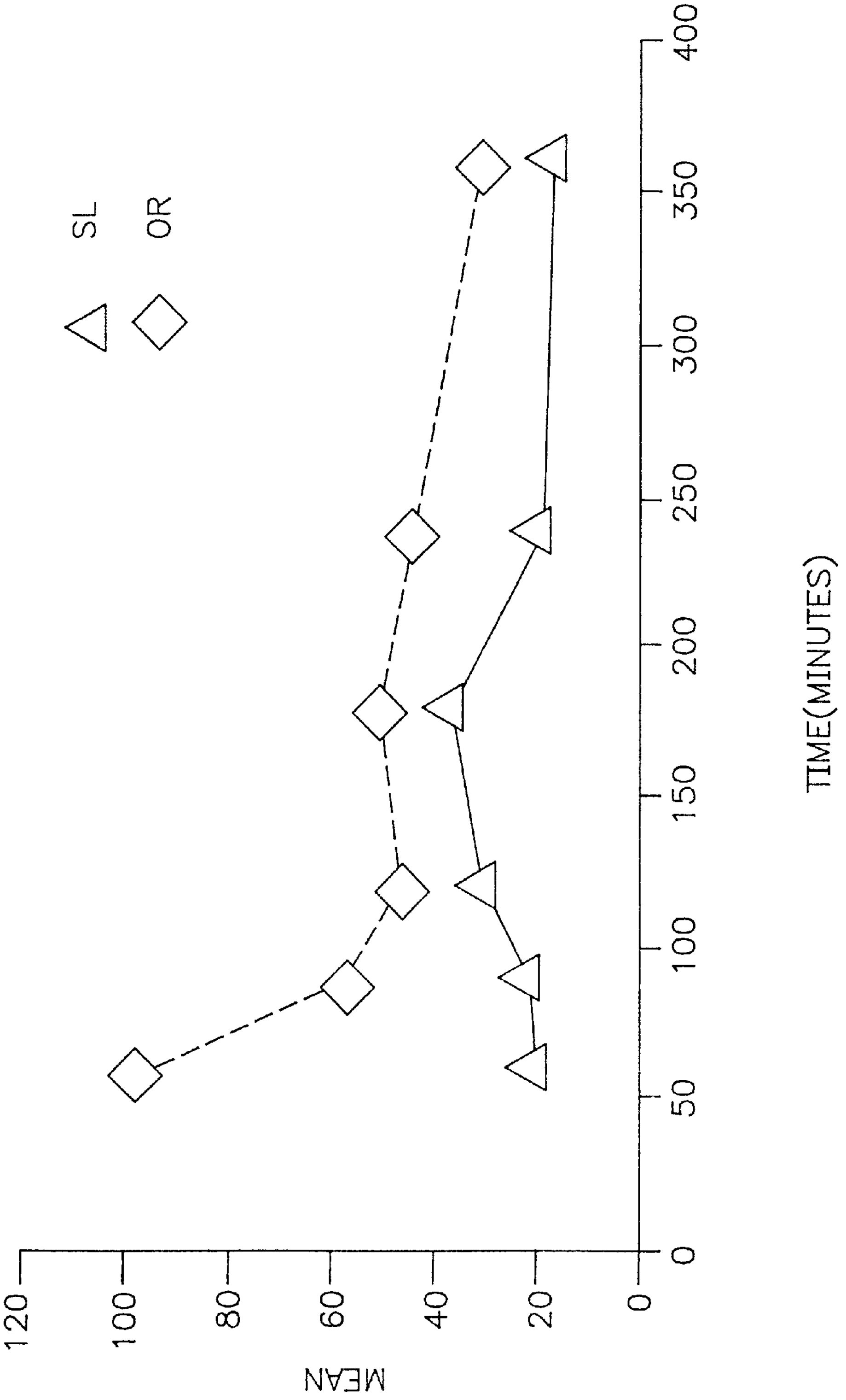
FIG. 11 is a graph illustrating the sublingual (SL) versus the oral (OR) dosing for m-chlorophenylpiperazine plasma.
Figure 12:
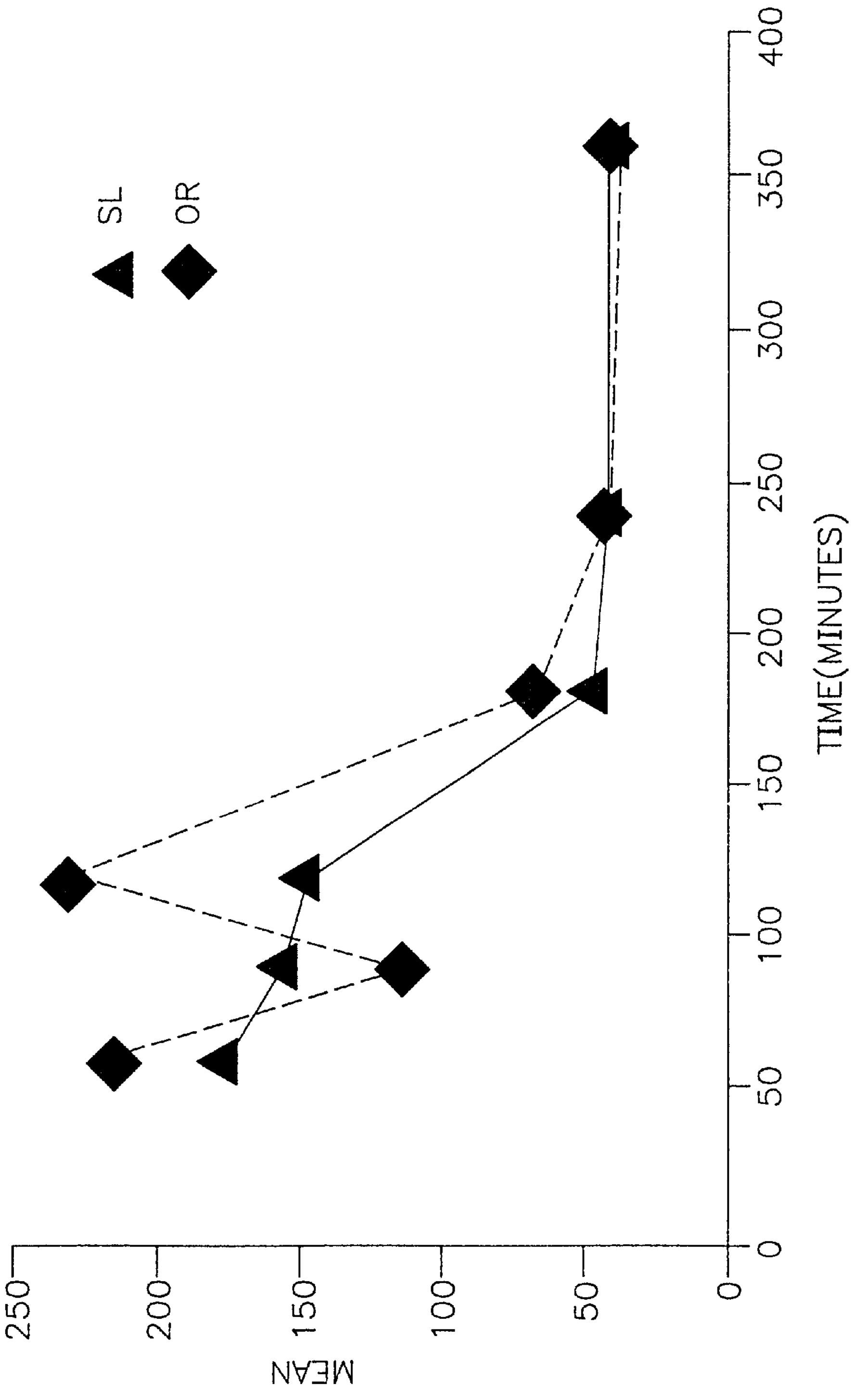
FIG. 12 is a graph illustrating the sublingual (SL) versus the oral (OR) dosing for nefazodone plasma.

At 1 hour, there was a 5 times greater ratio from oral as compared to sublingual administration for mCPP, which decreased to a 3 times greater ratio at 1 and ½ hours, and gradually reduced after that. (Also, see FIG. 11.) In contrast, the NEF levels were comparable in the ratios for oral as compared to sublingual administration. (Also, see FIG. 12.) Thus, the sublingual/oral ratio of NEF appeared slightly above 1.

Conditions such as obsessive compulsive syndrome and panic disorder, which have a large overlap with anxiety disorders, are susceptible to precipitation and worsening with mCPP. The present discovery indicates that mCPP, an unwanted metabolite of NEF, and especially the early peak mCPP levels, can be reduced by sublingual administration of NEF, and also should be reduced by buccal administration of NEF.

It has been demonstrated that mCPP, an unwanted metabolite, induces a rapid onset of adverse consequences and at times long-lasting adverse consequences, including obsessional ruminations and anxiety as reported by Zohar et al. With the present invention, it has been demonstrated that the rapid onset of mCPP maximal peak levels can be remarkably reduced by sublingual administration of NEF, and should also be reduced by buccal administration of NEF. This demonstration of changes with the mCPP metabolite of NEF is to be compared with the above data for trifluorobenzodiazepines and chlorimipramine, in which the accumulation of unwanted metabolites may require hours or days to manifest its effect, and with the rapid rise in plasma level of certain unwanted metabolites from oral administration mCPP that is associated with an intense, rapid induction of unwanted effects, the mCPP peak effects occurring within 3 hours, as reported by Zohar et al. Once precipitated, the adverse effects can last for hours.

Applicants submit that essentially the same results as discussed above for the sublingual administration of NEF will be obtained for the inhalation administration and/or skin administration of NEF.

In summary, the discovery that the sublingual method of administration for trifluorobenzodiazepines and propoxyphene reduced the adverse effects of unwanted metabolites was based on the reduction of the gradual accumulation of the unwanted metabolites to adverse cumulative concentration levels. Essentially the same results will occur for the inhalation method of administration and/or the skin method of administration for trifluorobenzodiazepines and propoxyphene.

On the other hand, in the case of mCPP, the unwanted metabolite levels measured after the oral administration of NEF far exceeded the 25 to 35 ng/ml of mCPP that manifests onset of adverse precipitous symptoms in susceptible panic disorder patients as reported by Zohar et al. More importantly, the ratio of peak oral to peak sublingual mCPP blood levels was found to be approximately 3 times that reported by Zohar et al. In contrast, the ratio of the parent compound, NEF, levels for the oral to sublingual ratio was found to be near 1 to 1.3 times that reported by Walsh et al. Essentially the same results will occur for the inhalation method of administration and/or the skin method of administration of NEF.

Also, trazodone, an antidepressant with a very close molecular structure to NEF, is similarly metabolized to the mCPP unwanted metabolite and is a candidate for sublingual or buccal administration to reduce the unwanted metabolite to parent drug ratio. In other words, sublingual or buccal administration of trazodone should increase the ratio of parent medicament to unwanted metabolite made available to the human body, including the central nervous system. Applicants submit that essentially the same results as discussed above for the sublingual administration of trazodone will be obtained for the inhalation administration and/or skin administration of trazodone.

It will be understood that various details of the invention may be changed without departing from the scope of the invention. Furthermore, the foregoing description is for the purpose of illustration only, and not for the purpose of limitation—the invention being defined by the claims.

What is claimed is:

1. In a method for administering medicament to the human body, including the central nervous system, wherein a therapeutically effective amount of said medicament is administered to a human, the improvement comprising the steps of:

(a) selecting a medicament that is metabolized into an unwanted or adversive metabolite that is increased by gastrointestinal tract absorption and subsequent portal vein entry to the liver, wherein the medicament is a trifluorobenzodiazepine;

(b) pacing the trifluorobenzodiazepine in an inhalation administration formulation;

(c) administering a therapeutically effective amount of the formulation from step (b) so as (i) to bypass the gastrointestinal tract absorption and subsequent portal vein entry to the liver and (ii) thereby to decrease formation of the unwanted metabolite;

(d) increasing the ratio of trifluorobenzodiazepine to the unwanted metabolite made available to the human body, including the central nervous system; and (e) utilizing this method over a period of one or more doses to achieve sustained high levels of the trifluorobenzodiazepine relative to the unwanted metabolite.

2. The method of claim 1, wherein the trifluorobenzodiazepine is selected from the group consisting of 7-chloro-1-(2,2,2-trifluoroethyl)-5-phenyl-1,3-dihydro-2H-1,4-benzodiazepine-2-one; 7-chloro-1-(2,2,2-trifluoroethyl)-5-phenyl-1,3-dihydro-3-hydroxy-2H-1,3-benzodiazepine-2-one; 7-chloro-1-(2,2,2-trifluoroethyl)-5-(2-fluorophenyl)-1,3-dihydro-2H-1,4-benzodiazepine-2-thione; 7-chloro-1-(2,2,2-trifluoroethyl)-5-(2-fluorophenyl)-1,3-dihydro-2H-1,4-benzodiazepine-2-one; 7-chloro-1-(2,2,2-trifluoroethyl)-5-(2-fluorophenyl)-1,3-dihydro-3-hydroxy-2H-1,4-benzodiazepine-2-one; 7-chloro-1-(2,2,2-trifluoroethyl)-5-(2-fluorophenyl)-1,3-dihydro-2H- 4-benzodiazepine; 7-chloro-1-(2,2,2-trifluoroethyl)-5-(2-chlorophenyl)-1,3-dihydro-2H-1,4-benzodiazepine; 7-bromo-1-(2,2,2-trifluoroethyl)-5-(2-fluorophenyl)-1,3-dihydro-2H-1,4-benzodiazepine; 7-chloro-1-(2,2,2-trifluoroethyl)-5-(2-fluorophenyl)-1,3-dihydro-3-hydroxy-2H-1,4-benzodiazepine-2-thione, and combinations thereof.

3. The method of claim 1, wherein the trifluorobenzodiazepine is lipid soluble.

4. The method of claim 1, wherein the inhalation administration formulation is selected from the group consisting of a nebulizer, a metered dose inhaler, a dry powder inhaler, a liposomal inhalator system, and combinations thereof.

* * * * *